(12) United States Patent
Hong et al.

(10) Patent No.: US 12,181,545 B2
(45) Date of Patent: Dec. 31, 2024

(54) MR COIL ASSEMBLY WITH MULTIPLE DIPOLE ANTENNAS AND CONNECTION ELEMENTS WITH BLOCKING CIRCUITS

(71) Applicant: Forschungszentrum Jülich GmbH, Jülich (DE)

(72) Inventors: Suk Min Hong, Würselen (DE); Nadim Joni Shah, Jülich (DE); Chang-Hoon Choi, Jülich (DE); Jörg Felder, Jülich (DE)

(73) Assignee: Forschungszentrum Jülich GmbH, Jülich (DE)

(*) Notice: Subject to any disclaimer, the term of this patent is extended or adjusted under 35 U.S.C. 154(b) by 657 days.

(21) Appl. No.: 17/434,220

(22) PCT Filed: Dec. 5, 2019

(86) PCT No.: PCT/EP2019/083857
§ 371 (c)(1),
(2) Date: Aug. 26, 2021

(87) PCT Pub. No.: WO2020/173590
PCT Pub. Date: Sep. 3, 2020

(65) Prior Publication Data
US 2022/0137165 A1     May 5, 2022

(30) Foreign Application Priority Data
Feb. 27, 2019   (DE) .............. 10 2019 105 021.9

(51) Int. Cl.
*G01R 33/36* (2006.01)
*A61B 5/055* (2006.01)
*G01R 33/34* (2006.01)

(52) U.S. Cl.
CPC ......... *G01R 33/3635* (2013.01); *A61B 5/055* (2013.01); *G01R 33/34076* (2013.01)

(58) Field of Classification Search
CPC ............ G01R 33/3635; G01R 33/3664; G01R 33/3415; A61B 5/055
(Continued)

(56) References Cited

U.S. PATENT DOCUMENTS 2,229,865 A    1/1941   Morgan
5,202,635 A    4/1993   Srinivasan et al.
(Continued)

FOREIGN PATENT DOCUMENTS

DE        4419730 C2 *    7/1999   ....... G01R 33/34053
DE      102010033322 A1 *  2/2012   ........... G01R 33/341
(Continued)

OTHER PUBLICATIONS

Matson, Gerald B., Peter Vermathen, and Tony C. Hill. "A practical double-tuned 1H/31P quadrature birdcage headcoil optimized for 31P operation." Magnetic Resonance in Medicine: An Official Journal of the International Society for Magnetic Resonance in Medicine 42.1 (1999): 173-182. (Year: 1999).*

(Continued)

*Primary Examiner* — Christopher P McAndrew
(74) *Attorney, Agent, or Firm* — CALDERON SAFRAN & WRIGHT P.C.

(57) ABSTRACT

A coil assembly for use as a transmission and/or receiving coil in an MR system comprises a dipole antenna assembly with multiple dipole antennas. Connection elements are converted from an electrically conductive state to an electrically non-conductive state. In the electrically conductive state, the dipole antennas form a cylindrical volume coil and/or a conductor loop assembly, in particular a flat conductor loop assembly. The connection elements comprise blocking circuits which automatically block when a high-frequency alternating voltage with a frequency correspond-
(Continued)

ing to the blocking frequency of the connection element blocking circuits is applied to the coil assembly.

29 Claims, 6 Drawing Sheets

(58) Field of Classification Search
USPC .......................................................... 324/318
See application file for complete search history.

(56) References Cited

U.S. PATENT DOCUMENTS

| | | | | |
|---|---|---|---|---|
| 5,363,845 | A * | 11/1994 | Chowdhury | A61B 5/708 324/318 |
| 5,462,055 | A | 10/1995 | Casey et al. | |
| 7,970,452 | B2 * | 6/2011 | Piron | A61B 90/14 5/601 |
| 9,874,615 | B2 | 1/2018 | Wiggins et al. | |
| 2008/0306377 | A1 * | 12/2008 | Piron | A61B 8/5238 324/318 |
| 2010/0253333 | A1 * | 10/2010 | Zhai | G01R 33/34076 324/318 |
| 2015/0005619 | A1 * | 1/2015 | LaViola | B29C 64/153 264/497 |
| 2015/0137815 | A1 * | 5/2015 | Lakshmanan | G01R 33/341 324/322 |
| 2017/0139019 | A1 * | 5/2017 | Kim | G01R 33/3657 |
| 2018/0321340 | A1 * | 11/2018 | Biber | G01R 33/34053 |

FOREIGN PATENT DOCUMENTS

| | | |
|---|---|---|
| JP | H06242202 A | 9/1994 |
| JP | 2004105753 A | 4/2004 |

OTHER PUBLICATIONS

Meyerspeer, Martin, et al. "An improved trap design for decoupling multinuclear RF coils." Magnetic resonance in medicine 72.2 (2014): 584-590. (Year: 2014).*

Alderman, Donald W. et al., "An efficient decoupler coil design which reduces heating in conductive samples in superconducting spectrometers", Journal of Magnetic Resonance (1969), Dec. 1979, vol. 36, No. 3, pp. 447-451, ISSN 0022-2364; https://doi.org/10.1016/0022-2364(79)90123-9.

Chin, Chih-Liang et al., "BirdcageBuilder: Design of Specified-Geometry Birdcage Coils with Desired Current Pattern and Resonant Frequency", Concepts Magn. Reson., Jun. 2002, vol. 15, No. 2, pp. 156-163. https://doi.org/10.1002/cmr.10030.

Duan, Yunsuo et al., "Computational and Experimental Optimization of a Double-Tuned 1H/31P Four-Ring Birdcage Head Coil for MRS at 3T," Journal of Magnetic Resonance Imaging, Jan. 2009, vol. 29, No. 1, pp. 13-22. https://doi.org/10.1002/jmri.21509.

Fitzsimmons, Jeffrey et al., "Double Resonant Quadrature Birdcage", Magn Reson Med., Jul. 1993, vol. 30, No. 1, pp. 107-111; https://doi.org/10.1002/mrm.1910300116.

Hong, Suk-Min et al., "New design concept of monopole antenna array for UHF 7T MRI", Magnetic Resonance in Medicine, May 2014, vol. 71, No. 5, pp. 1944-1952; https://doi.org/10.1002/mrm.24844.

Hong, Suk-Min et al. "Design and simulation of dual-band dipole antenna for 1H/31P at 9.4T MRf", Proceedings of the International Society for Magnetic Resonance in Medicine, ISMRM, Joint Annual Meeting ISMRM-ESMRMB, Paris, France, Jun. 16-21, 2018, No. 4400. Jun. 1, 2018 (Jun. 1, 2018); XP040703608.

Hong, Suk-Min et al. "Design of a Quadrature 1H/31P Coil Using Bent Dipole Antenna and Four-Channel Loop at 3T MRI", IEEE Transactions on Medical Imaging, Dec. 2018, vol. 37, No. 12, pp. 2613-2618, doi: 10.1109/TMI.2018.2844462.

Hudson, Alex M.J. et al., "Dual resonant birdcage coils for 1H detected 13C microscopic imaging at 11.7 T", Magnetic Resonance Materials in Physics, Biology and Medicine, Jun. 2000, vol. 10, No. 2, pp. 61-68, ISSN 1352-8661; https://doi.org/10.1007/BF02601839.

International Search Report mailed Mar. 16, 2020 from corresponding International Patent Application No. PCT/EP2019/083857; 11 pages.

Janzen, G., "Kurze Antennen. Entwurf und Berechnung verkürzter Sende—und Empfangsantennen," Kosmos Verlags GmbH, Jun. 1989, pp. 184-191 & 210-213; ISBN: 978-3440054697.

Matson, Gerald B. et al., "A practical double-tuned 1H/31P quadrature birdcage headcoil optimized for 31P operation", Magnetic Resonance in Medicine, vol. 42, Issue 1, pp. 173-182, Jul. 1999. https://doi.org/10.1002/(SICI)1522-2594(199907)42:1<173::AID-MRM23>3.0.CO;2-O.

Murphyboesch, J. et al., "Two Configurations of the Four-Ring Birdcage Coil for 1H Imaging and 1H-Decoupled 31P Spectroscopy of the Human Head", Journal of Magnetic Resonance, Series B, vol. 103, No. 2, Feb. 1994, pp. 103-114, ISSN 1064-1866; https://doi.org/10.1006/jmrb.1994.1017.

Perrier, A. L. et al., "Capacitive approach to restore decoupling between channels for four-element MR coil array", Electronics Letters, Jun. 2013, vol. 49, No. 13, pp. 815-816. https://doi.org/10.1049/el.2013.0447.

Raaijmakers, A. J. E. et al., "Design of a Radiative Surface Coil Array Element at 7 T: The Single-Side Adapted Dipole Antenna", Magnetic Resonance in Medicine, Nov. 2011, vol. 66, No. 5, pp. 1488-1497. http://dx.doi.org/10.1002/mrm.22886.

Schneider, H.J et al., "Crossed slotted tube resonator (CSTR)—a new double resonance NMR probehead", Review of Scientific Instruments, Jul. 1977, vol. 48, No. 7, pp. 832-834; https://doi.org/10.1063/1.1135166.

* cited by examiner

MR COIL ASSEMBLY WITH MULTIPLE DIPOLE ANTENNAS AND CONNECTION ELEMENTS WITH BLOCKING CIRCUITS

CROSS-REFERENCE TO RELATED APPLICATIONS AND CLAIM TO PRIORITY

This application is a national stage application of International Application No. PCT/EP2019/083857 filed Dec. 5, 2019, which claims priority to German Patent Application No. 10 2019 105 021.9 filed Feb. 27, 2019, the disclosures of which are incorporated herein by reference and to which priority is claimed.

FIELD OF THE INVENTION

The present invention relates to a coil arrangement for use as a transmitter and/or reception coil in an MR system, in particular an MRI and/or MRS system, which coil arrangement comprises a dipole antenna arrangement with a plurality of dipole antennas connected to one another via connecting elements, the connecting elements being designed to be transferred from an electrically connecting to an electrically disconnecting state and vice versa, and the arrangement being made in such a manner that the dipole antennas in the electrically connecting state of the connecting elements form at least a part of a preferably cylindrical volume coil and/or a conductor loop arrangement, in particular a flat conductor loop arrangement, of the coil arrangement comprising at least one conductor loop. Furthermore, the invention relates to an MR system, in particular MRI and/or MRS system, comprising such a coil arrangement. Furthermore, the invention relates to a use of such a coil arrangement.

BACKGROUND OF THE INVENTION

Magnetic resonance tomography, MRT for short, has been used in medical diagnostics for many years. MRT is an imaging method by means of which, in particular, the structure and function of tissue and organs can be depicted in the form of sectional images. MRT can also be referred to as MRI, which stands for "Magnetic Resonance Imaging". MRI is based on the active principles of nuclear spin resonance, or NMR, in particular field gradient NMR, and is therefore also known as nuclear spin imaging. The term NMR is a synonym for the term magnetic resonance, or MR. The abbreviation MRS stands for magnetic resonance spectroscopy. An MR system usually comprises a magnet, in particular a superconducting magnet, with a, for example, cylindrical coil arrangement, which is designed and/or set up to generate a static, preferably homogeneous, magnetic field $B_0$, which is preferably oriented along the axis of the cylindrical coil arrangement. Within a central opening of the magnet, there is a high-frequency coil arrangement which surrounds a receiving space in which a medium to be examined, in particular a person or a body part, for example the head of a person, is arranged during an MR examination in order to physically interact with the high-frequency coil arrangement. The high-frequency coil arrangement may be designed for both transmitting and receiving, or as a dedicated transmitting or receiving coil arrangement. In the following description of the principles of action, we refer to individual nuclear spins. This represents the classical description of quantum mechanical processes. By exposing the medium to be examined to the magnetic field $B_0$, nuclear spins of atomic nuclei of the medium are aligned in the direction of the magnetic field $B_0$, i.e. they experience a longitudinal magnetization in the direction of the magnetic field $B_0$. By means of the high-frequency coil arrangement, a high-frequency excitation pulse is now generated in the form of a time-limited high-frequency alternating electromagnetic field to which the medium to be examined is exposed, so that certain atomic nuclei of the medium under to be examined are excited by the high-frequency alternating electromagnetic field. For this purpose, the high-frequency electromagnetic alternating field has a frequency that is in resonance with the Lamor frequency $f_L$ of the atomic nuclei to be excited. The Lamor frequency $f_L$ is given by the following formula:

$$f_L = (\gamma B_0)/2\pi$$

Here, $\gamma$ is the gyromagnetic constant, which is constant for a given nuclear species. $B_0$ is the static magnetic field.

Excitation of atomic nuclei means that the magnetization of the nuclear spins is deflected, i.e. tilted from the direction of the $B_0$ field, i.e., from the equilibrium position. Thus, the longitudinal magnetization of the nuclear spins is at least partially converted into a transverse magnetization that is precessing about the field direction of the $B_0$ field. In this process, the nuclear spins precess at their Lamor frequency. The precessing transverse magnetization finally induces a high-frequency alternating electric voltage in a combined high-frequency transmitting and receiving coil arrangement or a dedicated high-frequency receiving coil arrangement, the frequency of which corresponds in particular to the Lamor frequency of the excited atomic nuclei to be observed or detected. Here, the amplitude of the induced AC voltage indicates the strength of the transverse magnetization. MRI is concerned with generating and displaying cross-sectional images of the spatial distribution of the transverse magnetization and/or resonance spectra. For this purpose, it is necessary to assign the classical NMR signals to specific spatial sections of the medium to be examined, i.e. to perform spatial coding. In MRI, this is done with the aid of time-varying magnetic gradient fields generated by gradient coils arranged in the aperture of the $B_0$ field magnet.

In classical MRI, imaging is based on the detection of $^1H$ nuclei, or hydrogen atom nuclei. Clinical MRI imaging is usually performed with a $B_0$ in the range of about 0.1 to 3.0 T. However, higher magnetic field strengths are increasingly being used, particularly in research. By means of so-called ultrahigh-field MRI, or UHF MRI for short, which works with a $B_0 \geq 7$ T, other atomic nuclei, so-called X-nuclei, can be efficiently detected in addition to the $^1H$ nuclei. Here, the "X" stands for any atomic nucleus with nuclear spin, except $^1H$. Examples of X-nuclei include, in particular, nuclei such as the $^{31}P$-nucleus and the $^{23}Na$-nucleus, which play an important role in physiological processes. X-nuclei, due to their much lower concentration compared to $^1H$ nuclei and their physical properties, usually provide a much weaker signal than $^1H$ nuclei, whose signal is also called proton signal. In UHF MRI, however, a comparatively high signal-to-noise ratio, comparatively high phase contrast, and comparatively high spectral resolution can be realized, in particular for the X-nuclei.

Efforts are therefore being made to create a high-frequency coil arrangement that is suitable for a so-called $^1H/X$-nucleus application, i.e., capable of exciting and/or detecting or observing different atomic nuclei. Thus, the coil arrangement must be sensitive to both $^1H$ nuclei and at least one X-nucleus. Specifically, the coil arrangement must be capable of radiating or receiving, on the one hand, a high-frequency alternating electromagnetic field resonant with the Lamor frequency $f_L$ of the $^1$H nuclei and, on the other hand, a high-frequency alternating electromagnetic field resonant with the Lamor frequency $f_L$ of a selected variety of X nuclei. The coil arrangement is then double-tuned, namely to two resonant frequencies, and/or double-resonant.

Different ways of tuning antennas or coil arrangements with antennas to specific frequencies have been known for a long time.

For example, U.S. Pat. No. 2,229,865 discloses a two-band dipole antenna and a double-resonant dipole antenna, respectively, whose electrical length can be varied by blocking circuits. The dipole antenna generates the double resonance by restricting standing waves between the blocking elements. In contrast, the entire length of the dipole antenna generates its natural standing wave current. Thus, the higher resonance uses only a portion of the physical conductor structure. For example, the required length of the dipole antenna to use it in the detection of X nuclei is about 125 cm for $^{31}$P nuclei at $B_0$=7 T and about 187 cm for $^{23}$Na nuclei at $B_0$=7 T. The use of a monofrequency dipole or monopole antenna arrangement in the detection of $^1$H nuclei is discussed by A. J. E. Raaijmakers, et al. in the paper "Design of a radiative surface coil array element at 7 T: the single-side adapted dipole antenna," Magn. Reson. Med. off. J. Soc. Magn. Reson. Med. Soc. Magn. Reson. Med. vol. 66, no. 5, pp. 1488-1497, November 2011, and by Hong Suk-Min, Park Joshua Haekyun, Woo MyungKyun, Kim Young-Bo, and Cho Zang-Hee in the paper "New design concept of monopole antenna array for UHF 7 T MRI," Magn. Reson. Med. vol. 71, no. 5, pp. 1944-1952, July 2013. Here, the required length of a dipole antenna is, for example, about 50 cm for $^1$H nuclei at $B_0$=7 T or about 37 cm for $^1$H nuclei at $B_0$=9.4 T. This length is close to a dimension suitable for head examinations and provides a relatively large penetration depth and more symmetric MRI relevant field component patterns compared to arrays of conductor loops. However, due to the relatively long length required for X-nuclei detection, the previously known two-band dipole antennas are not suitable for use in, for example, head MRI examinations.

Furthermore, coil arrangements comprising or consisting of a so-called volume coil are known. An example of a volume coil is the Alderman-Grant coil. This was described by D. W. Aldermann and D. M. Grant in the paper "An efficient decoupler coil design which reduces heating in conductive samples in superconducting spectrometers," J. Magn. Reson. 1969, vol. 36, no. 3, pp. 447-451, December 1979. It is capable of producing a relatively homogeneous magnetic field and is well suited for high field strengths. The Alderman-Grant coil consists of 2 or 4 rods, each connected at its ends by an end ring. Its operating principle is based on the use of symmetrical strip lines and goes back to the concept of the "slotted tube resonator" (Schneider and Dullenkopf, 1977). Another example of a volume coil is the so-called Birdcage coil, in particular a four- to eight-foot Birdcage coil, which may also include rings and bars.

For example, J. R. Fitzsimmons, B. L. Beck, and H. Ralph Brooker in the paper "Double resonant quadrature birdcage," Magn. Reson. Med, vol. 30, no. 1, pp. 107-114, Spring 1993, and by A. M. Hudson, W. Köckenberger, and R. W. Bowtell in the paper "Dual resonant birdcage coils for $^1$H detected 13C microscopic imaging at 11.7 T," Magma N. Y. N, vol., 10, no. 2, pp. 61-68, June 2000 each described a concentric arrangement of two physically separated birdcage coils. Here, one birdcage coil is tuned to a $^1$H core resonant frequency and the other birdcage coil is tuned to an X core resonant frequency. However, these coil arrangements have the disadvantage of having a greatly reduced signal-to-noise ratio for the upper resonant frequency compared to their mono-frequency implementations.

Doubly resonant or doubly tuned Birdcage coils are also known. For example, Y. Duan, B. S. Peterson, F. Liu, T. R. Brown, T. S. Ibrahim, and A. Kangarlu in the paper "Computational and experimental optimization of a double-tuned $^1$H/31P four-ring birdcage head coil for MRS at 3 T," J. Magn. Reson. Imaging, vol. 29, no. 1, pp. 13-22, spring 2009, and by J. Murphyboesch, R. Srinivasan, L. Carvajal, and T. R. Brown in the paper "Two Configurations of the Four-Ring Birdcage Coil for $^1$H Imaging and $^1$H-Decoupled 31P Spectroscopy of the Human Head," J. Magn. Reson. B, Vol. 103, No. 2, pp. 103-114, spring 1994 each described a doubly resonant Birdcage coil, more specifically a 4-ring Birdcage coil formed by doubling the end rings. Another double-resonant birdcage coil is described by G. B. Matson, P. Vermathen, and T. C. Hill in the paper "A parctical double-tuned $^1$H/31P quadrature birdcage headcoil optimized for 31P operation," Magn. Reson. Med, vol. 42, no. 1, pp. 173-182, spring 1999 described. In the latter birdcage coil, $^1$H blocking circuits are alternately placed, i.e., on every second rod.

When the aforementioned double-resonant Birdcage coils are used in MRI, especially RF MRI, the capacitance values for tuning, especially fine tuning, to the two resonant frequencies are very small. This is due in part to the high inductance value of the birdcage coil. For example, an 8-stage high-pass birdcage coil with a diameter of 26 cm and a length of 20 cm requires a capacitance of 2 pF. A 16-stage low-pass birdcage coil of the same diameter and length requires 0.36 pF of capacitance. At 300 MHz, the capacitance values required for tuning are approximately 0.5 pF. The previously mentioned capacitance values are in the range of common stray capacitances and/or parasitic capacitances. A calculation method for the capacitances in a Birdcage coil is described by C.-L. Chin, C. M. Collins, S. Li, B. J. Dardzinski, and M. B. Smith in the paper "BirdcageBuilder: Design of Specified-Geometry Birdcage Coils with Desired Current Pattern and Resonant Frequency," Concepts Magn. Reson. vol. 15, no. 2, pp. 156-163, June 2002. Thus, tuning of the previously known double-resonant Birdcage coils is extremely difficult.

Also disclosed in U.S. Pat. No. 5,462,055 is a coil arrangement for use in a combined MRI/hyperthermia system. The coil arrangement comprises a dipole antenna arrangement having a plurality of dipole antennas interconnected by connecting elements. In this regard, the connecting elements are configured to be converted from an electrically connecting state to an electrically disconnecting state, and vice versa. Specifically, the connecting elements are designed as transistor circuits comprising a transistor that is switched by applying appropriate control signals provided by a controller. In the electrically connected state of the connecting elements, the dipole antennas form part of a cylindrical volume coil of the coil arrangement. By switching the connecting elements between the two states, either MRI excitation energy or hyperthermia energy can be provided by means of the coil arrangement. More specifically, the volume coil is used for proton imaging, while the dipole antennas are used for hyperthermia excitation. In the coil arrangement of U.S. Pat. No. 5,462,055, switching the connecting elements between the electrically connecting and electrically disconnecting states is relatively costly, in particular because an additional control system must be provided.

SUMMARY OF THE INVENTION

Against this background, the present invention is based on the task of providing a coil arrangement of the type mentioned at the beginning, which is designed in such a way that it can be tuned and operated with less effort compared with the previously known coil arrangements.

According to the invention, this task is solved in a coil system of the aforementioned type in that the connecting elements comprise connecting element blocking circuits, which automatically block when a high-frequency AC voltage having a frequency corresponding to the blocking frequency of the connecting element blocking circuits is applied to the coil arrangement. In this case, the connecting element blocking circuits block as long as the high-frequency AC voltage of the blocking frequency is applied to the coil arrangement. The high-frequency AC voltage may also be a high-frequency AC voltage induced in the coil arrangement.

The invention is thus based on the consideration of providing the connecting elements of a coil arrangement with connecting element blocking circuits which automatically block when a high-frequency AC voltage with a frequency corresponding to the blocking frequency of the connecting element blocking circuits is applied to the coil arrangement, but otherwise do not block or at least do not block completely. Here, the blocking frequency is the frequency that cannot pass the respective connecting element blocking circuit. When the connecting element blocking circuits block, the connecting elements are in their electrically disconnecting state, which means that the dipole antennas are electrically disconnected from each other. The volume coil and/or conductor loop arrangement present in the electrically connecting state of the connecting elements is—when the blocking circuits block—then separated, so to speak, into individual dipole antennas, which in particular can work and/or be operated independently of each other. A coil comprises at least one conductor loop, i.e. in the simplest case it is a conductor loop. The conductor loop arrangement, in particular if it is flat, can be used, for example, in the examination of a spine. A coil arrangement with a flat conductor loop arrangement may be referred to as a surface coil arrangement. The volume coil may in particular be an Alderman-Grant or Birdcage coil. Due to the fact that the coil arrangement according to the invention uses connecting element blocking circuits to automatically, i.e. frequency-dependent, electrically connect or disconnect the dipole antennas, the coil arrangement according to the invention can be tuned and operated with less effort compared to the previously known coil arrangements and does not require any control of the connecting element blocking circuits. In contrast to active switches, which make or break connections in the time domain, the use of frequency-selective blocking circuits advantageously also allows the coil arrangement described herein to be used in so-called decoupling experiments using the Kern-Overhauser effect.

According to one embodiment of the invention, the coil arrangement is designed in such a way that the dipole antennas in the electrically disconnecting state of the connecting elements can radiate and/or receive a high-frequency electromagnetic alternating field with a first frequency, in particular corresponding to the blocking frequency, and that the volume coil resulting in the electrically connecting state of the connecting elements and/or each conductor loop of the conductor loop arrangement resulting in the electrically connecting state of the connecting elements can radiate and/or receive a high-frequency, electromagnetic alternating field with a second frequency different from the first. In particular, a doubly tuned coil arrangement is then present. The coil arrangement according to the invention makes it possible, in particular in high-field MRI, to use capacitors with capacitance values for fine tuning of the first and second radiation frequencies which are significantly larger and thus significantly more feasible than the capacitance values known from the prior art. In addition, coils with inductance values that are significantly easier to realize can be used. The first frequency can be a $^{1}$H-core resonant frequency, which means that the high-frequency, alternating electromagnetic field radiated and/or received up by the dipole antennas and/or a corresponding high-frequency alternating electric voltage induced in the coil arrangement is in resonance with the Lamor frequency of the $^{1}$H-cores for a certain $B_0$-field. In this case, standing waves are formed between the connecting element blocking circuits and within the individual dipole antennas, respectively, for $^{1}$H imaging. The second frequency can be an X-core resonant frequency, in particular a $^{31}$P-core or $^{23}$Na-core resonant frequency. This means that the high frequency alternating electromagnetic field radiated and/or received by the volume coil or each conductor loop of the conductor loop arrangement and/or a corresponding high frequency alternating electric voltage induced in the coil arrangement is resonant with the Lamor frequency of a particular X-core for a particular $B_0$ field. Thus, the X-core resonant frequency corresponds to the Lamor frequency of the X-cores. Thus, the conductor loops can each act as antennas for the X-core resonant frequency. By means of the coil arrangement, different electrical configurations for the two resonant frequencies can thus be provided by electrically separating or connecting the dipole antennas, both of which can be advantageously used for MRI examinations. The coil arrangement according to the invention is sensitive to two MRI cores without significant losses, and in particular does not require the use of lossy components. Therefore, compared to the previously known coil arrangements, the coil arrangement exhibits a high sensitivity, which is comparable to monofrequency arrangements, and thus a high signal-to-noise ratio, SNR, and efficiency for both resonant frequencies, i.e., for recordings from both cores. The connecting element blocking circuits are preferably so-called $^{1}$H connecting element blocking circuits, $^{1}$H blocking circuits for short, whose blocking frequency corresponds to a $^{1}$H core resonant frequency.

In general, for X-cores, the homogeneity becomes better the more dipole antennas are used. However, the number of dipole antennas is limited by the fact that above a certain number, the coupling of the dipole antennas in $^{1}$H operation is too high to be useful. A number of four to eight, in particular four or eight, dipole antennas has been found to be advantageous.

Advantageously, the dipole antennas each comprise a rod-shaped base element, to the axially opposite ends of which a conductor path segment, in particular in the form of a ring segment, adjoins, respectively. The axial ends of the rod-shaped base element adjoin the respective conductor path segment in particular centrally. Preferably, the conductor path segments of the dipole antennas are of the same size. In the case of ring-segment-like conductor path segments, these have in particular the same arc length. The rod-shaped base elements of the dipole antennas can be arranged at least substantially parallel to one another. Expediently, the rod-shaped base elements of the dipole antennas are arranged uniformly spaced from one another in the circumferential direction of the volume coil or in the longitudinal direction of the conductor loop arrangement. The length of the rod-shaped base elements of the dipole antennas, the height of the volume coil or the width of the conductor loop arrangement can be in the range from 25 to 30 cm, in particular 25 cm or 28 cm, in particular for examinations of the human head. Preferably, the length of the dipole antenna is matched to the connecting element blocking frequency. Measures for varying the physical length of dipole antennas, e.g., by introducing concentrated components, are known to those skilled in the art and are described, inter alia, in G. Janzen, "Kurze Antennen. Entwurf und Berechnung verkürzter Sende-und Empfangsantennen," Kosmos Verlags GmbH, June 1989, ISBN: 978-3440054697.

According to a further embodiment, the conductor path segments of the dipole antennas are connected to one another other via the connecting elements to form two conductor paths, in particular two annularly closed conductor paths. In particular, in the case of two conductor paths closed in a ring, the number of connecting elements per conductor path can correspond to the number of dipole antennas. In particular, in the case of a flat conductor loop arrangement, the number of connecting elements per conductor path is preferably one less than the number of dipole antennas. The diameter of the annularly closed conductor paths or the volume coil can be in the range from 25 to 30 cm, in particular 26 cm, in particular for measurements on the human head.

According to a further advantageous embodiment, at least one of the connecting element blocking circuits comprises a connecting element coil and a connecting element capacitor, which are connected in parallel. The connecting element coil preferably has an inductance in the range from 38 to 41 nH, particularly preferably in the range from 39 to 40 nH, in particular of 39 nH or 40 nH. The connecting element capacitor preferably has a capacitance in the range from 6 to 8 pF, in particular of 6.8 pF. At least one connecting element may comprise a second connecting element capacitor, which is connected in series with the connecting element blocking circuit. The second connecting element capacitor preferably has a capacitance in the range from 5 to 50 pF, more preferably in the range from 8.2 to 40 pF, in particular of 8.2 pF or 40 pF. Expediently, the second connecting element capacitor is designed, in particular has a suitable capacitance, to tune, in particular fine-tune, the coil arrangement to the second frequency. A capacitance value of the second connecting element capacitor in the order of magnitude mentioned above is easily realizable, which contributes to the fact that the coil arrangement can be tuned with relatively little effort. The aforementioned capacitance and inductance values are particularly advantageous when using the coil arrangement as part of an MR system comprising a magnet configured to generate a magnetic field $B_0$ of 7 T.

In a preferred embodiment, the rod-shaped base elements of the dipole antennas are each separated centrally to form two poles of the respective dipole antenna. Advantageously, the rod-shaped base elements of the dipole antennas are each provided with a junction device for connecting to an AC voltage supply and/or scanning device, which comprises electrical junction elements connected to the two poles of the dipole antenna. Preferably, the rod-shaped base elements are each provided with the junction device in their central section. A $^1$H-core signal can be fed via the electrical junction elements of the junction devices in each case, in particular the respective dipole antenna can be fed with a high-frequency alternating voltage whose frequency preferably corresponds to a $^1$H-core resonant frequency, in order to cause the dipole antennas to radiate a high-frequency alternating electromagnetic field with the $^1$H-core resonant frequency, respectively. When the frequency of the fed high-frequency AC voltage corresponds to the blocking frequency of the connecting element blocking circuits, an AC electric current corresponding to the fed high-frequency AC voltage is isolated on the respective dipole antenna. A high-frequency AC voltage induced in the coil arrangement can also be tapped and/or received via the electrical junction elements of the junction devices, respectively.

The coil arrangement can be designed in such a way that a feed and/or a tap of $^1$H-core signals and/or X-core signals can take place via the electrical junction elements of at least one junction device, in particular of all junction devices. Here, the term "$^1$H-core signals" includes both a high-frequency alternating voltage fed into the coil arrangement, the frequency of which corresponds to the $^1$H-core resonant frequency, and a high-frequency alternating electrical voltage tapped at the coil arrangement, induced in the coil arrangement due to excited $^1$H-cores, the frequency of which corresponds in particular to the $^1$H-core resonant frequency. The term "X-core signals" includes both a high-frequency alternating electric voltage fed into the coil arrangement, the frequency of which is different from the $^1$H-core resonant frequency and preferably corresponds to an X-core resonant frequency, and a high-frequency alternating electric voltage tapped at the coil arrangement, induced due to excited X-cores in the coil arrangement, the frequency of which corresponds in particular to the X-core resonant frequency.

Advantageously, the coil arrangement is designed in such a way that it can be operated in a 4-channel and/or 2-channel quadrature mode. In 4-channel quadrature mode, the X-core signal or the $^1$H-core signal is fed in/tapped at four junction devices, whereas in 2-channel quadrature mode, the X-core signal or the $^1$H-core signal is fed in/tapped at two junction devices. Quadrature operation enables the generation of a circularly polarized field. By generating a circular field polarization, the required transmitting power is reduced and the receive SNR is increased compared to linear field polarization.

According to a preferred embodiment, the coil arrangement is designed in such a way that a feed and/or tap of X-core signals can take place via the electrical junction elements of a pair of two adjacent junction devices, in particular adjacent in the circumferential direction of the volume coil, of a total of four junction devices. The coil arrangement can be designed in such a way that the volume coil and/or conductor loop arrangement resulting in the electrically connecting state of the connecting elements can be fed via the two adjacent junction devices in quadrature mode with a high-frequency alternating voltage, whose frequency differs from the $^1$H-core resonant frequency and preferably corresponds to an X-core resonant frequency in order to cause the volume coil or each conductor loop of the conductor loop arrangement to radiate a high-frequency alternating electromagnetic field having an X-core resonant frequency. In this case, the two adjacent junction devices can be driven with signals that are 90 degrees out of phase. In the case of a feed to four junction devices, which is known in MRI as a "four port drive" and also enables the generation of a circularly polarized field distribution, the phase relationship between the feed signals is preferably 0-90-180-270 degrees.

If a conductor loop arrangement results in the electrically connecting state of the connecting elements, a feed and/or a tap of $^1$H-core signals and/or X-core signals can also take place at the free ends of the two conductor paths.

A dipole capacitor can be provided in the center of a dipole antenna between the two poles, which dipole capacitor is in particular part of the junction device. The term "dipole capacitor" is used here merely to distinguish it from the other capacitors, and the prefix "dipole-" has no functional meaning. The dipole capacitor preferably has a capacitance of 0 pF. The dipole capacitors can also have capacitance values deviating from 0 pF in order to achieve improved impedance matching, in particular to a connected transmission line. Expediently, the dipole capacitor is designed, in particular has a suitable capacitance, to tune, in particular fine-tune, the coil arrangement to the first frequency.

According to a further embodiment, a coupling element is provided, in particular connected in parallel with the dipole capacitor, which is electrically connected to the two poles of the dipole antenna and bridges them. Here, the coupling element is designed to be transferred from an electrically connecting to an electrically disconnecting state, and vice versa. Preferably, the coupling element is part of the junction device. Preferably, the coupling element comprises a coupling element blocking circuit, which automatically blocks when a high-frequency AC voltage with a frequency corresponding to the blocking frequency of the coupling element blocking circuit is applied to or induced in the coil arrangement, in particular to the electrical junction elements of the junction device of the corresponding dipole antenna. Here, the blocking frequency of the coupling element blocking circuit corresponds in particular to the first frequency. The blocking frequencies of the connecting element blocking circuits and the coupling element blocking circuits preferably coincide. The coupling element blocking circuit blocks as long as the high-frequency AC voltage of the blocking frequency is applied to the coil arrangement.

Advantageously, at least one of the coupling element blocking circuits comprises a coupling element coil and a coupling element capacitor, which are connected in parallel. Here, the coupling element coil preferably has an inductance in the range from 38 to 41 nH, particularly preferably in the range from 39 to 40 nH, in particular 39 nH or 40 nH. The coupling element capacitor preferably has a capacitance in the range from 6 to 8 pF, in particular of 6.8 pF. At least one coupling element may comprise a second coupling element capacitor, which is connected in series with the coupling element blocking circuit of the coupling element. Preferably, the second coupling element capacitor has a capacitance in the range from 20 to 110 pF, more preferably in the range from 33 to 100 pF, in particular of 33 pF, 95 pF or 100 pF. Expediently, the second coupling element capacitor is designed, in particular has a suitable capacitance, to tune, in particular fine-tune, the coil arrangement to the second frequency and/or to trigger a short circuit at the second frequency. A capacitance value of the coupling element capacitor and the second coupling element capacitor in the order of magnitude mentioned above is easily realizable, which contributes to the fact that the coil arrangement can be tuned with relatively little effort. The aforementioned capacitance and inductance values are particularly advantageous when using the coil arrangement as part of an MR system that includes a magnet configured to generate a $B_0$ of 7 T.

A further embodiment of the invention is characterized in that the axial ends of the rod-shaped base element of at least one dipole antenna each connect to the respective conductor path segment of the dipole antenna with the interposition of a junction point capacitor. The junction point capacitor preferably has a capacitance in the range from 10 to 40 pF, particularly preferably in the range from 18 to 32 pF, in particular of 18 pF or 32 pF. Advantageously, the junction point capacitor is designed, in particular has a suitable capacitance, to tune, in particular fine-tune, the coil arrangement to the second frequency. The junction point capacitors thus form a further degree of freedom in the tuning, in particular if other capacitors, which are preferably also provided for tuning, are already determined by boundary conditions.

Preferably, the coil arrangement is tuned, in particular by means of the second connecting element capacitors and/or the second coupling element capacitors and/or the dipole capacitors and/or the junction point capacitors, in such a way that each dipole antenna in the electrically disconnecting state of the connecting elements and in particular of the coupling elements can radiate and/or receive a high-frequency electromagnetic alternating field with a $^1$H-core resonant frequency, and the volume coil resulting in the electrically connecting state of the connecting elements and in particular of the coupling elements and/or each conductor loop of the conductor loop arrangement resulting in the electrically connecting state of the connecting elements and in particular of the coupling elements can radiate and/or receive a high-frequency electromagnetic alternating field with an X-core resonant frequency.

Table 1 below lists advantageous capacitance and inductance values of the electrical components of a junction device for a $^1$H/$^{31}$P tuning at $B_0$=7 T. The corresponding capacitance and inductance values for a $^1$H/$^{23}$Na tuning at $B_0$=7 T are given in parentheses behind each. Here, $^1$H/$^{31}$P tuning stands for tuning to the $^1$H-core resonant frequency of 300 MHz and the $^{31}$P-core resonant frequency of 120 MHz as the X-core resonant frequency at $B_0$=7 T. $^1$H/$^{23}$Na tuning correspondingly represents tuning to the $^1$H core resonant frequency of 300 MHz and the $^{23}$Na core resonant frequency of 78.82 MHz as the X-core resonant frequency at $B_0$=7 T.

TABLE 1

| Coupling element coil Inductance [nH] | Coupling element capacitor Capacitance [pF] | Dipole capacitor Capacitance [pF] | Second coupling element capacitor Capacitance [pF] |
| --- | --- | --- | --- |
| 40 (39) | 6.8 (6.8) | 0 (0) | 33 oder 100 (33 oder 95) |

If the dipole antenna arrangement comprises four dipole antennas, the second coupling element capacitors of the coupling elements of the junction devices of two adjacent dipole antennas, in particular two dipole antennas adjacent in the circumferential direction of the volume coil, each have an equal capacitance of in particular 33 pF and the second coupling element capacitors of the two remaining dipole antennas likewise have an equal capacitance of preferably 100 pF in particular for the $^1$H/$^{31}$P tuning or 95 pF in particular for the $^1$H/$^{23}$Na tuning at $B_0$=7 T. Preferably, the two junction devices whose coupling element capacitors have a capacitance of 33 pF are two junction devices that are not used for feeding/tapping an X-core signal.

Table 2 below lists advantageous capacitance and inductance values of the electrical components of a connecting element for the $^1$H/$^{31}$P tuning described above and in parentheses for the $^1$H/$^{23}$Na tuning described above, respectively.

TABLE 2

| Connecting element coil Inductance [nH] | Connecting element capacitor Capacitance [pF] | Second connecting element capacitor Capacitance [pF] |
|---|---|---|
| 40 (39) | 6.8 (6.8) | 8.2 (40) |

The junction point capacitors may each have a capacitance of 18 pF for the $^1$H/$^{31}$P tuning and a capacitance of 32 pF for the $^1$H/$^{23}$Na tuning.

If a conductor loop arrangement results in the electrically connecting state of the connecting elements and in particular the coupling elements, each conductor loop of the conductor loop arrangement can be formed at least by parts of two adjacent dipole antennas. The conductor loop arrangement preferably comprises several conductor loops, in particular three conductor loops. At least one part of a dipole antenna, in particular, if present, at least its rod-shaped base element and preferably, if present, two junction point capacitors thereof, may form a part of two adjacent conductor loops. In this case, two conductor loops then practically "share" at least part of a dipole antenna, in particular, if present, the rod-shaped base element and the two junction point capacitors thereof. If at least a part of a dipole antenna forms a part of two adjacent conductor loops, the capacitance values of the connecting element capacitors and/or of the second connecting element capacitors and/or of the coupling element capacitors and/or of the second coupling element capacitors and/or of the dipole capacitors and/or of the junction point capacitors and/or of further capacitors within the conductor loop arrangement are preferably selected in such a manner that adjacent conductor loops are preferably capacitively decoupled. The determination of the capacitance values required to decouple adjacent conductor loops is described by A. L. Perrier, D. Grenier, N. Ravel, P. Litaudon and O. Beuf in the paper "Capacitive approach to restore decoupling between channels for four-element MR coil array," ELECTRONICS LETTERS, Jun. 20, 2013, Vol. 49, No. 13.

It is understood that the coil arrangement according to the invention may be suitable for use as a transmitter and/or reception coil in a UHF MRI system.

According to the invention, the aforementioned task is also solved by an MR system, in particular MRI, preferably high-field/ultra-high-field MRI, and/or MRS, preferably high-field/ultra-high-field MRS system with the coil arrangement according to the invention described above.

The MR system preferably comprises a magnet, in particular a superconducting magnet, which is designed to generate a static, preferably homogeneous magnetic field $B_0$, where $B_0$ is preferably 7 T. The coil arrangement may be located within a central opening of the magnet. The coil arrangement may surround a receiving space in which a medium to be examined is or may be arranged during an MR examination.

Furthermore, the invention relates to a use of the coil arrangement according to the invention described above as a high frequency transmitter and/or reception coil in magnetic resonance imaging, in particular high field/ultra high field magnetic resonance imaging and/or magnetic resonance spectroscopy, in particular high field/ultra high field magnetic resonance spectroscopy.

BRIEF DESCRIPTION OF THE DRAWINGS

Further features and advantages of the present invention will become apparent from the following description of an embodiment of a coil arrangement according to the present invention, with reference to the accompanying drawing. Therein is.

DETAILED DESCRIPTION OF THE PREFERRED EMBODIMENT(S)

Figure 1:
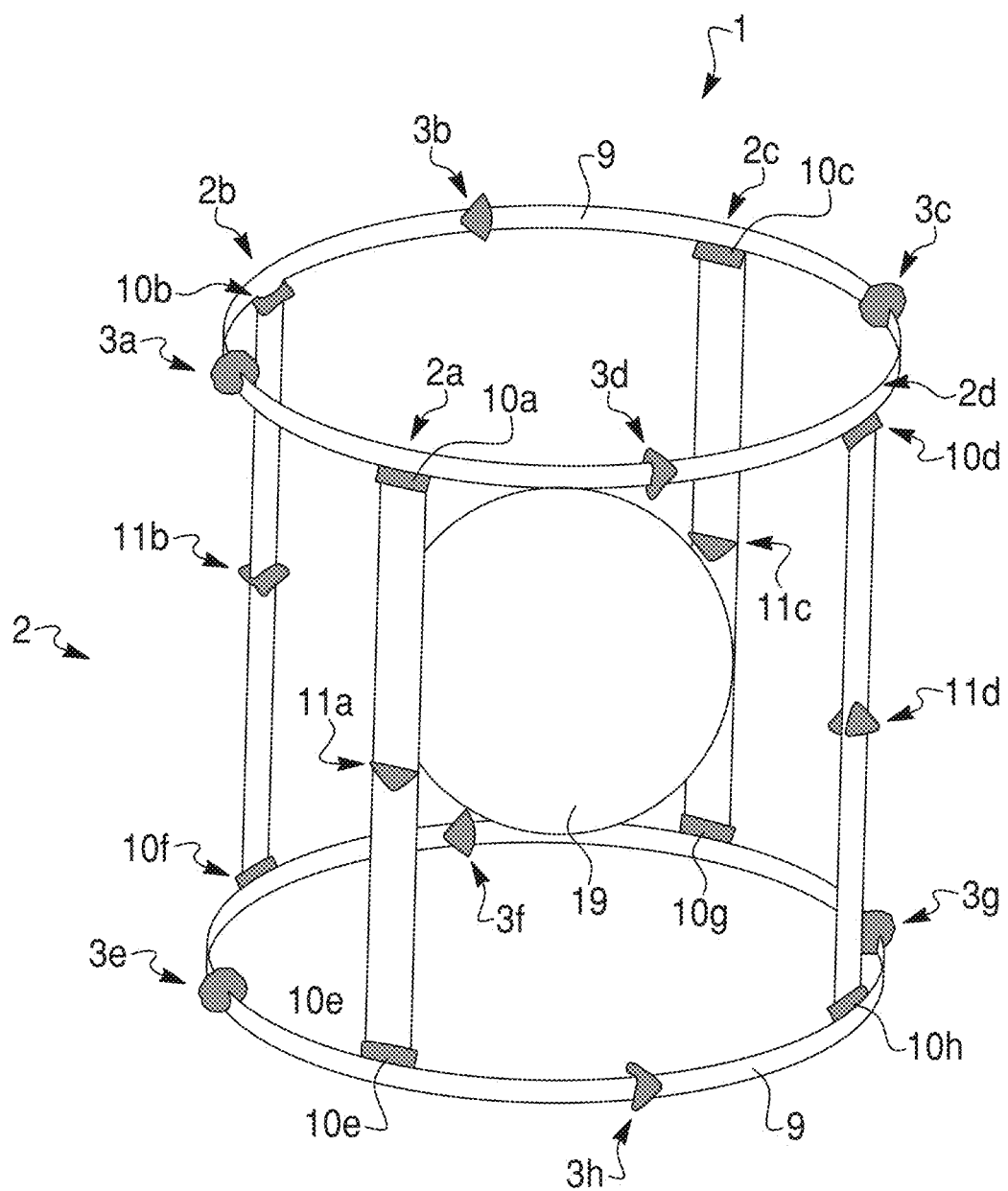
FIG. 1 a schematic perspective view of a coil arrangement according to an embodiment of the present invention.
Figure 2:
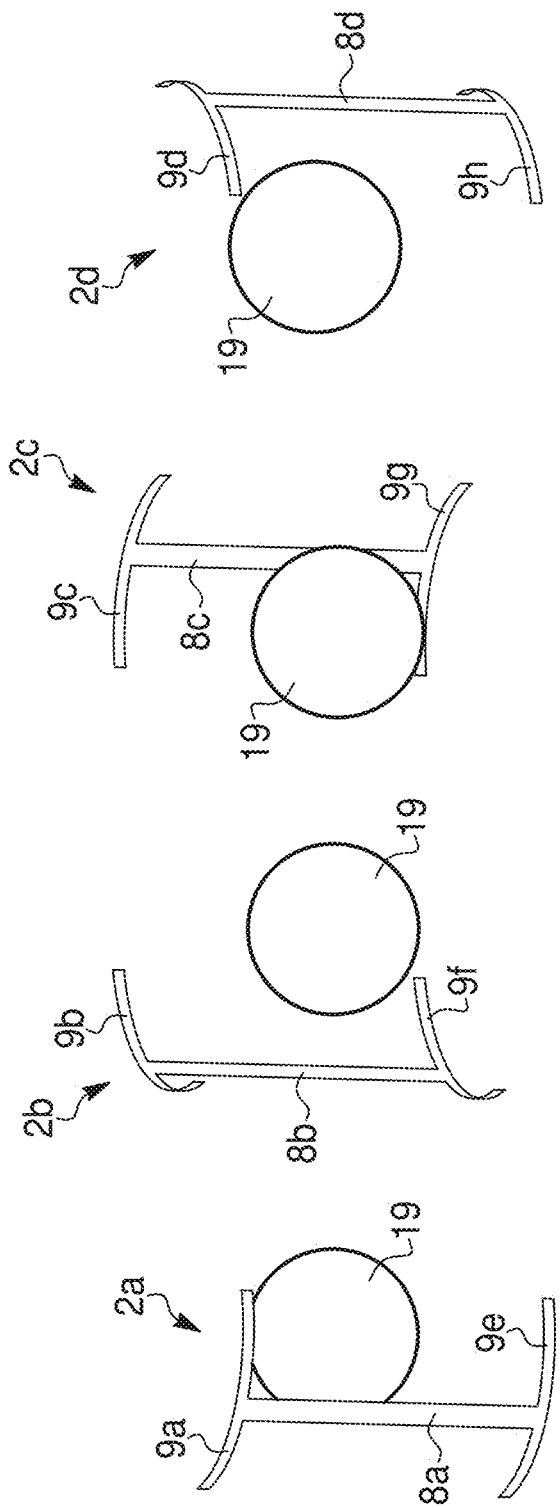
FIG. 2 a kind of exploded view of the coil arrangement of FIG. 1, in which the dipole antennas are shown separated.

FIG. 1 shows a schematic view of a coil arrangement 1 according to an embodiment of the present invention. The coil arrangement 1 comprises a dipole antenna arrangement 2 with four dipole antennas 2a-d, which are interconnected by eight connecting elements 3a-h. FIG. 2 shows a kind of exploded view of the coil arrangement 1, in which the dipole antennas 2a-d are shown separately. The connecting elements 3a-h are designed to be transferred from an electrically connecting to an electrically disconnecting state, and vice versa. The arrangement is recognizably made such that the dipole antennas 2a-d form a cylindrical volume coil in the electrically connecting state of the connecting elements 3a-h.

Figure 3:
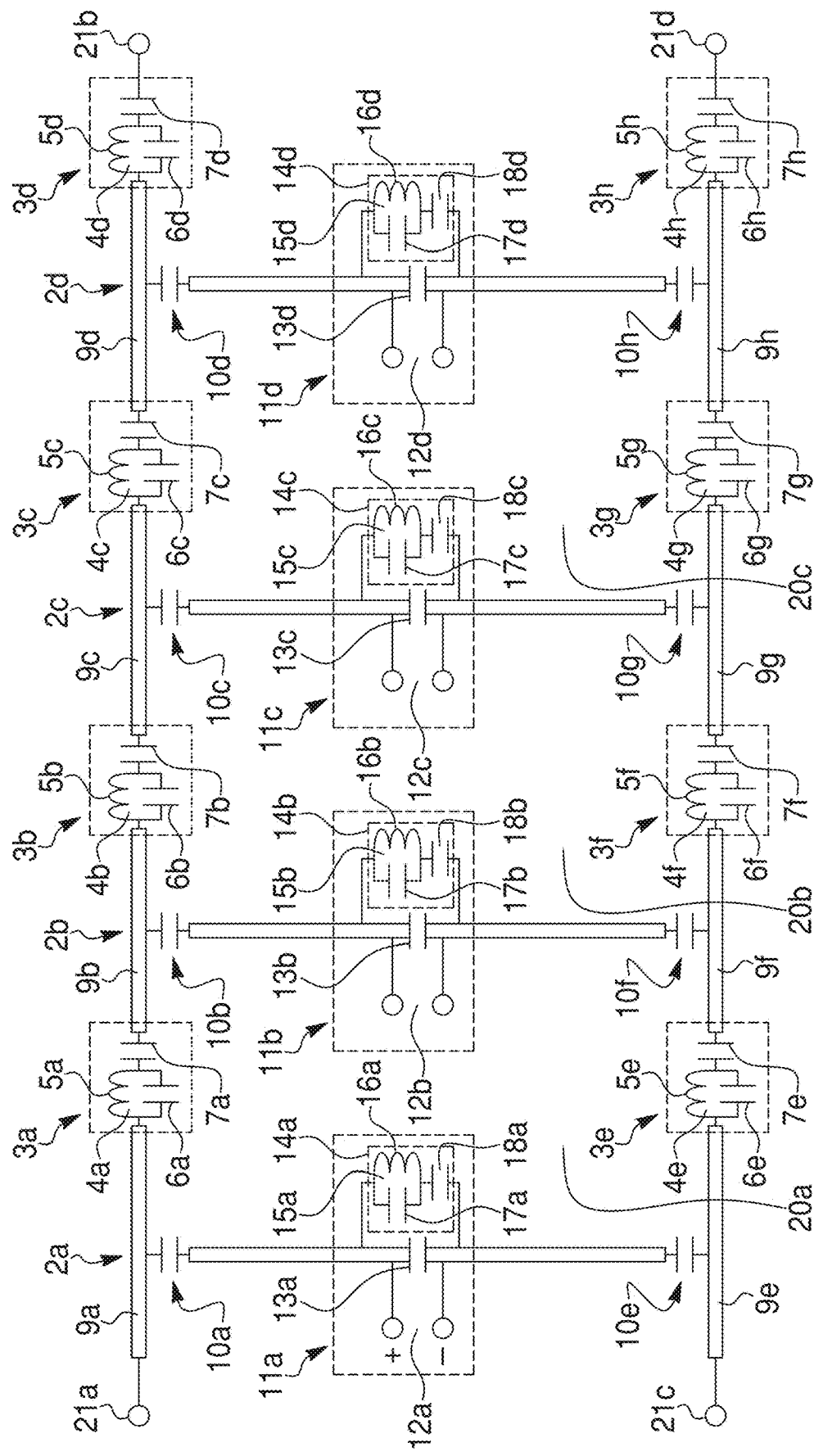
FIG. 3 a circuit diagram of the coil arrangement of FIG. 1.

The connecting elements 3a-h each comprise a connecting element blocking circuit 4a-h which automatically blocks when a high-frequency AC voltage having a frequency corresponding to the blocking frequency of the connecting element blocking circuits 4a-h is applied to and/or induced in the coil arrangement 1. This can be seen in the circuit diagram of the coil arrangement 1 shown in FIG. 3. The connecting element blocking circuits 4a-h each comprise a connecting element coil 5ah and a connecting element capacitor 6a-h, which are connected in parallel. In addition, each connecting element 3a-h includes a second connecting element capacitor 7a-h connected in series with the connecting element blocking circuit 4a-h.

The dipole antennas 2a-d each have a rod-shaped base element 8a-d, at the axially opposite ends of which a ring-segment-like conductor path segment 9a-h adjoins, respectively. The axial ends of the rod-shaped base element 8a-d adjoin to the center of the respective conductor path segment 9a-h with the interposition of a junction point capacitor 10a-h. The rod-shaped base elements 8a-d of the dipole antennas 2a-d are arranged parallel to each other and evenly spaced from each other in the circumferential direction of the volume coil. The conductor loop segments 9a-h are of the same size, or more precisely, have the same arc length. Moreover, the ring-segment-like conductor path segments 9a-h are connected to each other via the connecting elements 3a-h to form two conductor paths 9 closed in a ring shape. Thus, four connecting elements 3a-h are arranged in each conductor path 9.

The rod-shaped base elements 8a-d of the dipole antennas 2a-d are each separated centrally to form two poles of the respective dipole antenna 2a-d. In addition, the rod-shaped base elements 8a-d are each provided in their central section with a junction device 11a-d for connection to an AC voltage supply and receiving device not shown. The junction device 11a-d comprises electrical junction elements 12a-d connected to the two poles of the dipole antenna 2a-d. Furthermore, the junction device 11a-d comprises a dipole capacitor 13a-d provided at the center of the dipole antenna 2a-d between the two poles. Furthermore, the junction device 11a-d comprises a coupling element 14a-d connected in parallel to the dipole capacitor 13a-d, which is electrically connected to the two poles of the dipole antenna 2a-d and bridges them. The total of four coupling elements 14a-d are each designed to be transferred from an electrically connecting state to an electrically disconnecting state, and vice versa. For this purpose, the coupling elements 14a-d each include a coupling element blocking circuit 15a-d having a coupling element coil 16a-d and a coupling element capacitor 17a-d connected in parallel. The coupling element blocking circuits 15a-d automatically block when a high-frequency AC voltage having a frequency corresponding to the blocking frequency of the coupling element blocking circuits 15a-d is applied to and/or induced in the coil arrangement 1. Further, the coupling elements 14a-d each include a second coupling element capacitor 18a-d connected in series with the coupling element blocking circuit 15a-d.

The cylindrical volume coil resulting in the electrically connecting state of the coupling elements 3a-h is an Alderman-Grant type volume coil with two end rings, here the ring-shaped closed conductor paths 9, and four webs, here the rod-shaped base elements 8a-d of the dipole antennas 2a-d. The coil arrangement 1 is 28 cm long in the present case and has a diameter of 26 cm in the present case. FIGS. 1 and 2 show a spherical phantom 19 within the coil arrangement 1. This is representative of a body part to be examined, in particular a human or animal head to be examined.

In the following table, the electrical components of the four junction devices 11a-d are briefly described again and their values are listed.

| Junction device | Coupling element coil 16a-d Description | Value (nH) | Coupling element capacitor 17a-d Description | Value (pF) | Dipole-capacitor 13a-d Description | Value (pF) | Second coupling element capacitor 18a-d Description | Value (pF) |
|---|---|---|---|---|---|---|---|---|
| 11a | Coil 16a for $^1$H coupling element blocking circuit 15a | 40 | Capacitor 17a for $^1$H coupling element blocking circuit 15a | 6.8 | Capacitor 13a for dipole tuning | 0 | Capacitor 18a for tuning that triggers short-circuit at X-core frequency | 33 |
| 11b | Coil 16b for $^1$H coupling element blocking circuit 15b | 40 | Capacitor 17b for $^1$H coupling element blocking circuit 15b | 6.8 | Capacitor 13b for dipole tuning | 0 | Capacitor 18b for tuning that triggers short-circuit at X-core frequency | 33 |
| 11c | Coil 16c for $^1$H coupling element blocking circuit 15c | 40 | Capacitor 17c for $^1$H coupling element blocking circuit 15c | 6.8 | Capacitor 13c for dipole tuning | 0 | Capacitor 18c for X-core tuning | 100 |
| 11d | Coil 16d for $^1$H coupling element blocking circuit 15d | 40 | Capacitor 17d for $^1$H coupling element blocking circuit 15d | 6.8 | Capacitor 13d for dipole tuning | 0 | Capacitor 18d for X-core tuning | 100 |

In the following table the electrical components of the eight connecting elements 3a-h are again briefly described and their values are listed.

| Connecting elements | Connecting element coil 5a-h Description | Value (nH) | Connecting element capacitor 6a-h Description | Value (pF) | Second connecting element capacitor 7a-h Description | Value (pF) |
|---|---|---|---|---|---|---|
| 3a | Coil 5a for $^1$H-Connecting element blocking circuit 4a | 40 | Capacitor 6a for $^1$H-Connecting element blocking circuit 4a | 6.8 | Tuning for X-cores | 8.2 |

-continued

| Connecting elements | Connecting element coil 5a-h Description | Value (nH) | Connecting element capacitor 6a-h Description | Value (pF) | Second connecting element capacitor 7a-h Description | Value (pF) |
|---|---|---|---|---|---|---|
| 3b | Coil 5b for $^1$H-Connecting element blocking circuit 4b | 40 | Capacitor 6b for $^1$H-Connecting element blocking circuit 4b | 6.8 | Tuning for X-cores | 8.2 |
| 3c | Coil 5c for $^1$H-Connecting element blocking circuit 4c | 40 | Capacitor 6c for $^1$H-Connecting element blocking circuit 4c | 6.8 | Tuning for X-cores | 8.2 |
| 3d | Coil 5d for $^1$H-Connecting element blocking circuit 4d | 40 | Capacitor 6d for $^1$H-Connecting element blocking circuit 4d | 6.8 | Tuning for X-cores | 8.2 |
| 3e | Coil 5e for $^1$H-Connecting element blocking circuit 4e | 40 | Capacitor 6e for $^1$H-Connecting element blocking circuit 4e | 6.8 | Tuning for X-cores | 8.2 |
| 3f | Coil 5f for $^1$H-Connecting element blocking circuit 4f | 40 | Capacitor 6f for $^1$H-Connecting element blocking circuit 4f | 6.8 | Tuning for X-cores | 8.2 |
| 3g | Coil 5g for $^1$H-Connecting element blocking circuit 4g | 40 | Capacitor 6g for $^1$H-Connecting element blocking circuit 4g | 6.8 | Tuning for X-cores | 8.2 |
| 3h | Coil 5h for $^1$H-Connecting element blocking circuit 4h | 40 | Capacitor 6h for $^1$H-Connecting element blocking circuit 4h | 6.8 | Tuning for X-cores | 8.2 |

Figure 4:
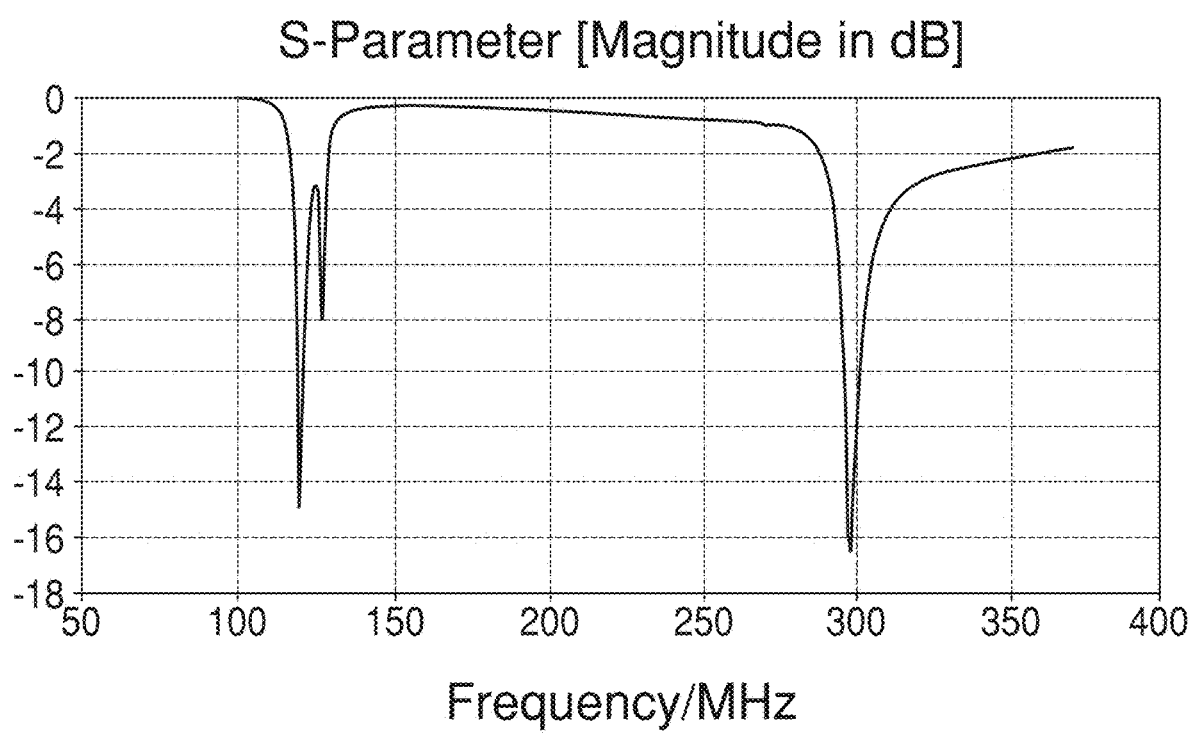
FIG. 4 a frequency spectrum of the input reflection coefficient illustrating the two resonant frequencies to which the coil arrangement according to the invention is tuned.

FIG. 4 shows a frequency spectrum of the input reflection coefficient of the coil arrangement 1 according to the invention, which is tuned by the capacitance and inductance values listed in the above tables. The junction point capacitors 10a-h and, in particular, also the connecting element coils 5a-h and the coupling element coils 16a-d also contribute to the tuning. In the present case, the capacitance of the junction point capacitors 10a-h is 18 pF each. It can be seen that the coil system is doubly tuned at $B_0=7$ T, namely to the $^1$H-core resonant frequency of 300 MHz and to an X-core resonant frequency, namely the $^{31}$P-core resonant frequency of 120 MHz.

When the coil arrangement 1 according to the invention, which is doubly tuned in the manner described above, is used in an MRI system with $B_0=7$ T, the dipole antennas 2a-d are each supplied with a high-frequency alternating voltage via the electrical junction elements 12a-d of their junction devices 11a-d in a first operating mode of the MRI system. Here, the phase relationship between the feed signals applied to the four junction devices 11a-d may be, for example, 0-90-180-270 degrees. The frequency of the high-frequency AC voltage corresponds to a common blocking frequency of the connecting element blocking circuits 4a-h and the coupling element blocking circuits 15a-d. Here, the common blocking frequency corresponds to the $^1$H core resonance frequency. Thereupon, the connecting element blocking circuits 4a-h and the coupling element blocking circuits 15a-d automatically block, thereby transferring the connecting elements 3a-h and the coupling elements 14a-d to their electrically disconnecting state. In the electrically disconnecting state, each dipole antenna 2a-d radiates a high-frequency alternating electromagnetic field with the $^1$H-core resonant frequency of 300 MHz. Later, a high-frequency alternating electric voltage induced due to excited $^1$H nuclei in the coil arrangement 1 is tapped at the junction devices 11a-d.

In a second operating mode of the MRI system, the coil arrangement 1 is supplied with a high-frequency AC voltage via the electrical junction elements 12c and 12d of the two junction devices 11c and 11d adjacent to each other in the circumferential direction of the volume coil in a quadrature mode, wherein the junction devices 11c and 11d are driven with signals phase-shifted by 90 degrees. Here, the frequency of the high-frequency AC voltage is different from the common blocking frequency. Thus, the connecting elements 3a-h and the coupling elements 14a-d are in their electrically connecting state. Thereupon, the volume coil resulting in the electrically connecting state radiates a high-frequency alternating electromagnetic field with the $^{31}$P core resonance frequency of 120 MHz. Later, an AC electric voltage induced due to excited $^{31}$P cores in the coil arrangement 1 is tapped at the junction devices 11c and 11d.

The coil arrangement 1 according to the invention described above was used as a high-frequency coil in an MRI system.

Figure 5:
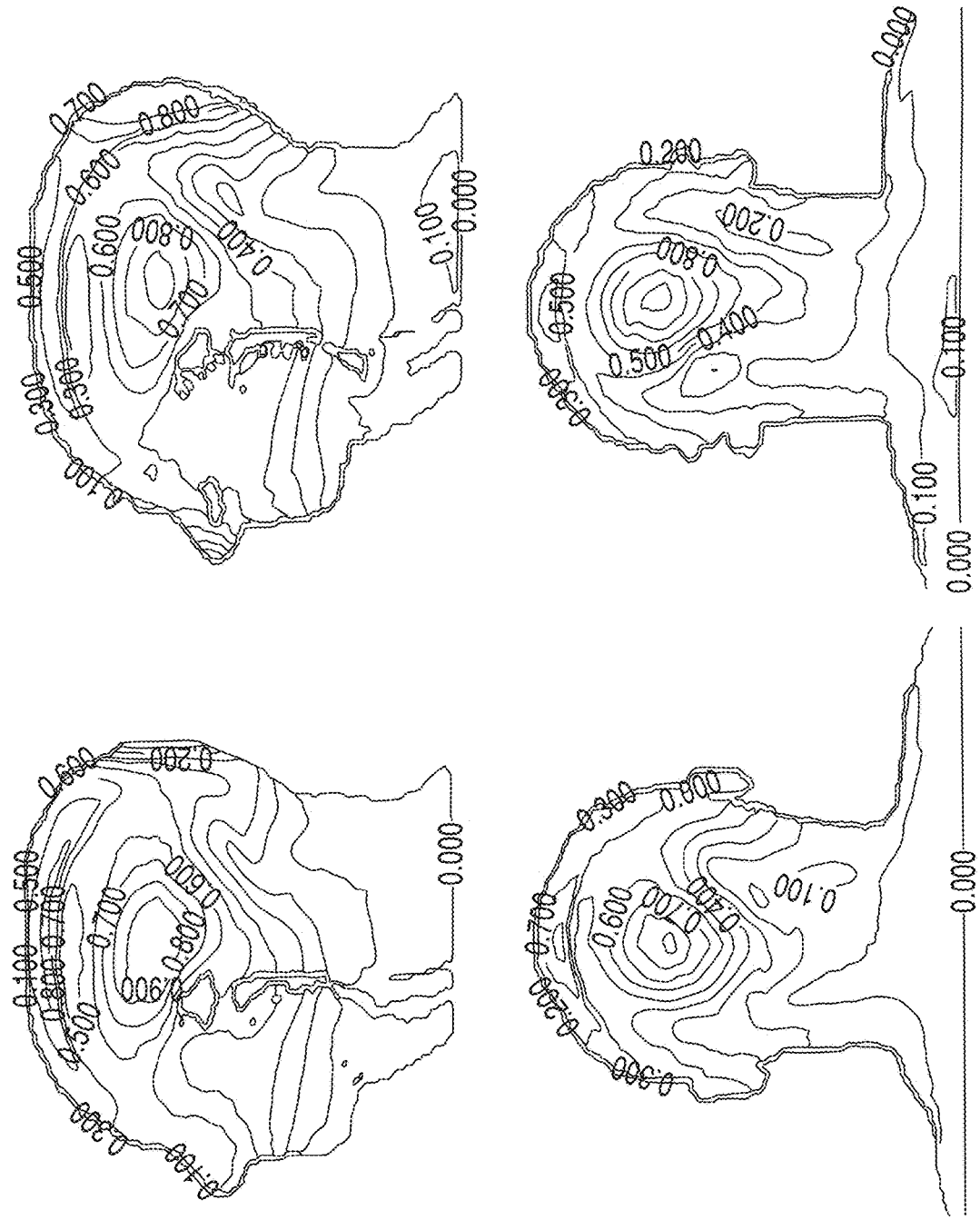
FIG. 5 a graphical representation of the safe transmission efficiency of the coil arrangement according to the invention compared with the safe transmission efficiency of a simply tuned 8-channel loop arrangement at the $^1$H core resonant frequency of 300 MHz.

The electromagnetic field distribution in the head of a subject was first simulated in the case where the $^1$H nuclei were excited and subsequently detected. With $B_0=7$ T, the $^1$H-nucleus resonance frequency and $^1$H-nucleus Lamor frequency, respectively, were 300 MHz. The same MRI study was performed again with a comparison arrangement using an 8-channel coil arrangement tuned only to the $^1$H-nucleus resonant frequency as the high-frequency coil. Specifically, in the comparison arrangement, eight conductor loops were placed around the subject's head. The simply tuned 8-channel arrangement provided a quasi-optimal comparison measurement for a $^1$H examination. The resulting MRI sectional images using both the coil arrangement 1 according to the invention and the comparison arrangement are shown in FIG. 5 in matrix form. In the left column are the sectional images for the comparison arrangement and in the right column are the sectional images for the coil arrangement 1 according to the invention. The top row shows the sectional views in the sagittal plane and the bottom row shows the sectional views in the frontal or coronal plane. Specifically, a comparison of the safe transmission efficiency of both MRI examinations is shown. Here, the safe transmission efficiency is defined as the amplitude of the circularly polarized radiofrequency excitation field divided by the maximum specific absorption rate $B_1^+/\sqrt{SAR}$. The comparison shows that the safe transmission efficiency using the coil arrangement 1 according to the invention with a mean value of 0.48 $\mu T/\sqrt{w}$ over the brain of the test person and the safe transmission efficiency using the comparison arrangement with a mean value of 0.51 $\mu T/\sqrt{w}$, which can be regarded as quasi-optimal, are similar, although the coil arrangement 1 according to the invention is a double-tuned or double-resonant coil arrangement. This indicates only a small loss.

Figure 6:
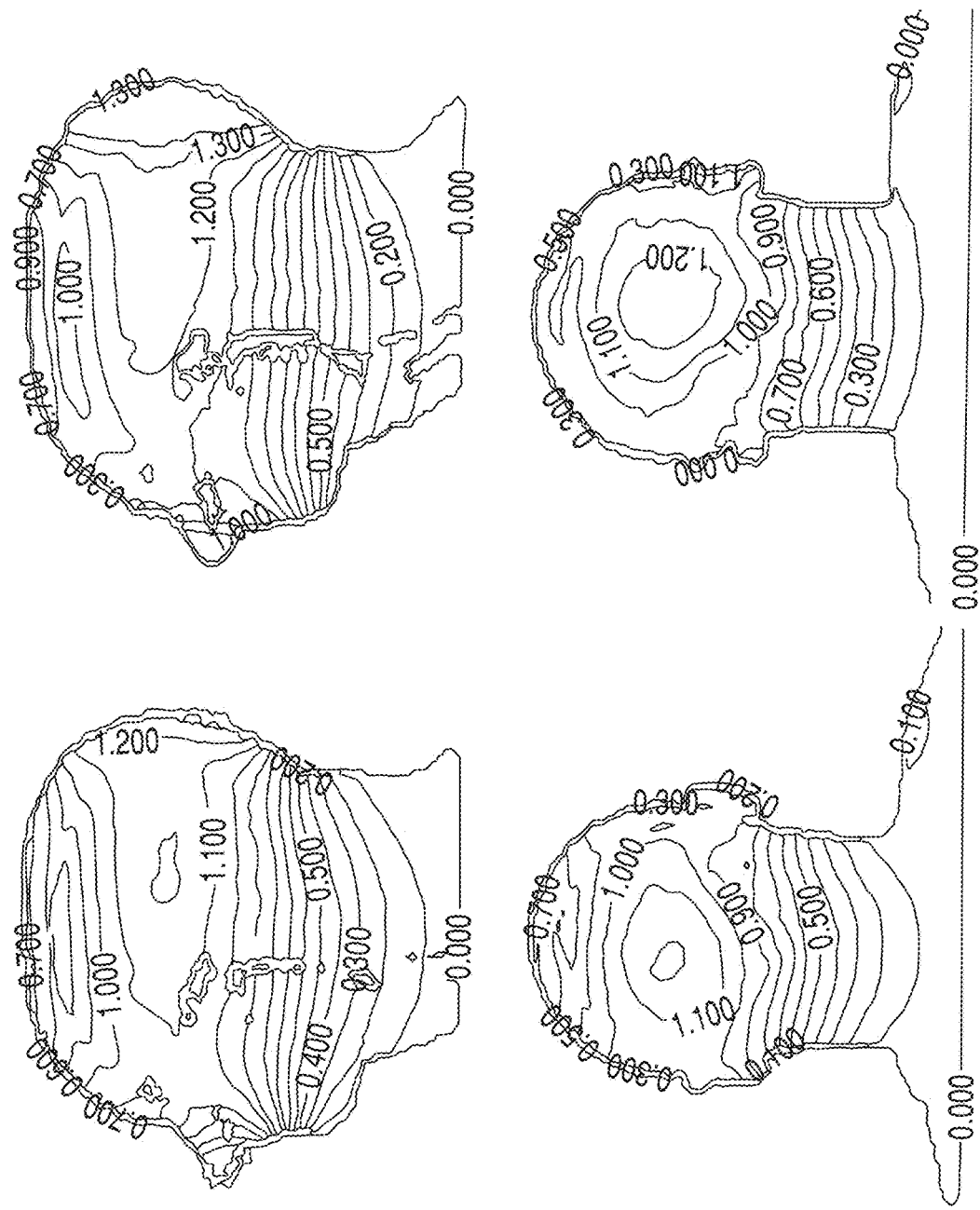
FIG. 6 a graphical representation of the safe transmission efficiency of the coil arrangement of the invention compared with the safe transmission efficiency of a single-tuned birdcage coil at the $^{31}$P core resonant frequency of 120 MHz.

In addition, a simulation of the field distribution in the head of a subject was carried out in which the $^{31}$P nuclei were excited and subsequently detected. With $B_0$=7 T, the $^{31}$P-nucleus resonance frequency and $^{31}$P-nucleus Lamor frequency, respectively, were 120 MHz. The same MRI study was performed again with a comparison setup using a birdcage coil as the high-frequency coil, which was tuned only to the $^{31}$P-core resonant frequency. The single-tuned birdcage coil provided a quasi-optimal comparison measurement for a $^{31}$P examination. The resulting MRI sectional images using both the coil arrangement 1 according to the invention and the comparison arrangement are shown in FIG. 6 in matrix form. In the right column are the sectional images for the coil arrangement 1 according to the invention and in the left column are the sectional images for the comparison arrangement. The top row shows the sectional views in the sagittal plane and the bottom row shows the sectional views in the frontal or coronal plane. The presented comparison of the safe transmission efficiency of both MRI examinations shows that the safe transmission efficiency when using the coil arrangement 1 according to the invention with a mean value of 1.09 $\mu T/\sqrt{w}$ over the brain of the subject and the safe transmission efficiency when using the comparison arrangement with a mean value of 1.00 $\mu T/\sqrt{w}$, which can be regarded as quasi-optimal, are similar, although the coil arrangement 1 according to the invention is a double-tuned or double-resonant coil arrangement. This indicates only a small loss.

In the previously described embodiment of a coil arrangement 1 according to the invention, the electrically connecting state of the connecting elements 3*a-h* and the coupling elements 14*a-d* results in a volume coil. In an alternative embodiment, instead of a volume coil, a flat conductor loop arrangement may result, which may, for example, have a flat structure similar to the embodiment of FIG. 3, but without the two connecting elements 3*d* and 3*h*. In this case, the conductor loop arrangement comprises three conductor loops 20*a-c*, each formed by at least parts of two adjacent dipole antennas 2*a-d*. In the present example, a portion of dipole antenna 2*b* forms both a portion of conductor loop 20*a* and a portion of conductor loop 20*b*. Also, a portion of the dipole antenna 2*c* forms both a portion of the conductor loop 20*b* and a portion of the conductor loop 20*c*. More specifically, the conductor loop 20*a* is formed by the rod-shaped base element 8*a*, the two junction point capacitors 10*a* and 10*e*, and one half of each of the conductor path segments 9*a* and 9*e* of the dipole antenna 2*a*, and the rod-shaped base element 8*b*, the two junction point capacitors 10*b* and 10*f*, and one half of each of the conductor loop segments 9*b* and 9*f* of the dipole antenna 2*b*. The conductor loop 20*b* is formed by the rod-shaped base element 8*b*, the two junction point capacitors 10*b* and 10*f*, and one half of each of the conductor path segments 9*b* and 9*f* of the dipole antenna 2*b*, and the rod-shaped base element 8*c*, the two junction point capacitors 10*c* and 10*g*, and one half of each of the conductor path segments 9*c* and 9*g* of the dipole antenna 2*c*. Lastly, the conductor loop 20*c* is formed by the rod-shaped base element 8*c*, the two junction point capacitors 10*c* and 10*g*, and one half each of the conductor path segments 9*c* and 9*g* of the dipole antenna 2*c*, and the rod-shaped base element 8*d*, the two junction point capacitors 10*d* and 10*h*, and one half each of the conductor path segments 9*d* and 9*h* of the dipole antenna 2*d*. Thus, the conductor loops 20*a* and 20*b* "share" the rod-shaped base element 8*b* and the two junction point capacitors 10*b* and 10*f* of the dipole antenna 2*b*. The conductor loops 20*b* and 20*c* "share" the rod-shaped base element 8*c* and the two junction point capacitors 10*c* and 10*g* of the dipole antenna 2*c*. The capacitance values of all capacitors within the conductor loop arrangement are selected such that adjacent conductor loops 20*a-c* are preferably capacitively decoupled.

In the case of a flat conductor loop arrangement, the two conductor loops 2 are preferably straight and not ring-shaped. A feed and/or a tap of $^1$H-core and/or X-core signals can take place via the free ends 21*a-d* of the conductor loops as an alternative to the junction devices 11*a-d* in the case of a flat conductor loop arrangement. In the case of a flat conductor loop arrangement, the radiation and/or reception of the high-frequency, electromagnetic alternating field with the X-core resonant frequency takes place via the individual conductor loops 20*a-c*. The radiation and/or the reception of the high-frequency, electromagnetic alternating field with the $^1$H-core resonant frequency takes place via the individual dipole antennas 2*a-d*.

LIST OF REFERENCE SIGNS

1 coil arrangement
2 dipole antenna arrangement
2*a-d* dipole antennas
3*a-h* connecting elements
4*a-h* connecting element blocking circuit
5*a-h* connecting element coil
6*a-h* connecting element capacitor
7*a-h* second connecting element capacitor
8*a-d* rod-shaped base element
9 conductor path
9*a-h* conductor path segment
10*a-h* junction point capacitor
11*a-d* junction device
12*a-d* junction element
13*a-d* dipole capacitor
14*a-d* coupling element 15a-d coupling element blocking circuit
16a-d coupling element coil
17a-d coupling element capacitor
18a-d second coupling element capacitor
19 phantom
20a-c conductor loop
21 free end

The invention claimed is:

1. A coil arrangement (1) for use as a transmitter and/or reception coil in an MR system, the coil arrangement (1) comprising a dipole antenna arrangement (2) with a plurality of dipole antennas (2a-d) connected to one another via connecting elements (3a-h), the connecting elements (3a-h) being designed to be transferred from an electrically connecting state to an electrically disconnecting state, and vice versa, and the arrangement configured so that the dipole antennas (2a-d) in the electrically connecting state of the connecting elements (3a-h) form at least a part of a volume coil and/or a conductor loop arrangement of the coil arrangement (1) comprising conductor loops (20a-c),
    wherein the connecting elements (3a-h) comprise connecting element blocking circuits (4a-h), which automatically block when a high-frequency AC voltage having a frequency corresponding to the blocking frequency of the connecting element blocking circuits (4a-h) is applied to the coil arrangement (1),
    wherein the coil arrangement (1) is configured so that the dipole antennas (2a-d) radiate and/or receive a high-frequency electromagnetic alternating field with a first frequency being the blocking frequency, when the connecting elements (3a-h) are in the electrically disconnecting state,
    wherein the volume coil resulting in the electrically connecting state of the connecting elements (3a-h) and/or each of the conductor loops (20a-c) of the conductor loop arrangement resulting in the electrically connecting state of the connecting elements (3a-h) radiates and/or receives a high-frequency, electromagnetic alternating field with a second frequency different from the first frequency, and
    wherein the first frequency is a $^1$H-core resonant frequency and the second frequency is an X-core resonant frequency.

2. The coil arrangement (1) according to claim 1, wherein the second frequency is a $^{31}$P-core resonant frequency or $^{23}$Na-core resonant frequency.

3. The coil arrangement (1) according to claim 1, wherein each of the dipole antennas (2a-d) comprises a rod-shaped base element (8a-d), at the axially opposite ends of which a conductor path segment (9a-h) adjoins respectively, the axial ends of the rod-shaped base element (8a-d) adjoining the respective conductor path segment (9a-h), and the conductor path segments (9a-h) of the dipole antennas (2a-d).

4. The coil arrangement (1) according to claim 3, wherein the rod-shaped base elements (8a-d) of the dipole antennas (2a-d) are arranged at least substantially parallel to one another and/or the rod-shaped base elements (8a-d) of the dipole antennas (2a-d) are arranged uniformly spaced apart from one another in the circumferential direction of the volume coil or in the longitudinal direction of the conductor loop arrangement and/or the length of the rod-shaped base elements (8a-d) of the dipole antennas (2a-d), the height of the volume coil or the width of the conductor loop arrangement is in the range from 25 to 30 cm.

5. The coil arrangement (1) according to claim 3, wherein the conductor path segments (9a-h) of the dipole antennas (2a-d) are connected to one another via the connecting elements (3a-h) to form two conductor paths (9).

6. The coil arrangement (1) according to claim 1, wherein at least one of the connecting element blocking circuits (4a-h) comprises a connecting element coil (5a-h) and a connecting element capacitor (6a-h), which are connected in parallel, wherein the connecting element coil (5a-h) has an inductance from 38 to 41 nH, and/or the connecting element capacitor (6a-h) has a capacitance from 6 to 8 pF.

7. The coil arrangement (1) according to claim 6, wherein at least one connecting element (3a-h) comprises a second connecting element capacitor (7a-h) which is connected in series with the connecting element blocking circuit (4a-h), the second connecting element capacitor (7a-h) having a capacitance from 5 to 50 pF.

8. The coil arrangement (1) according to claim 7, wherein the second connecting element capacitor (7a-h) is configured to tune the coil arrangement (1) to the second frequency.

9. The coil arrangement (1) according to claim 3, wherein the rod-shaped base elements (8a-d) of the dipole antennas (2a-d) are each separated to form two poles of the respective dipole antenna (2a-d).

10. The coil arrangement (1) according to claim 9, wherein the rod-shaped base elements (8a-d) of the dipole antennas (2a-d) have a junction device (11a-d) for connection to an AC voltage supply and/or scanning device, which comprises electrical junction elements (12a-d) connected to the two poles of the dipole antenna (2a-d).

11. The coil arrangement (1) according to claim 2, wherein the coil arrangement (1) is configured so that a feed and/or a tap of $^1$H-core signals and/or X-core signals can take place via the electrical junction elements (12a-d) of at least one junction device (11a-d).

12. The coil arrangement (1) according to claim 1, wherein the coil arrangement (1) is configured to be operated in a 4-channel and/or 2-channel quadrature mode.

13. The coil arrangement (1) according to claim 11, wherein the coil arrangement (1) is configured so that least one of a feed of X-core signal and a tap of X-core signals can take place via the electrical junction elements (12a-d) of a pair of two adjacent junction devices (11a-d).

14. The coil arrangement (1) according to claim 13, wherein the coil arrangement (1) is configured so that the volume coil and/or conductor loop arrangement resulting in the electrically connecting state of the connecting elements (3a-h) can be fed via the two adjacent junction devices (11a-d) in quadrature mode with a high-frequency AC voltage, whose frequency differs from the 1H-core resonant frequency and corresponds to an X-core resonant frequency in order to cause the volume coil or each conductor loop (20a-c) of the conductor loop arrangement to radiate a high-frequency alternating electromagnetic field having an X-core resonant frequency.

15. The coil arrangement (1) according to claim 9, wherein a dipole capacitor (13a-d) is in the center of a dipole antenna (2a-d) between the two poles, wherein the dipole capacitor (13a-d) is part of the junction device (11a-d), and wherein the dipole capacitor (13a-d) has a capacitance of 0 pF.

16. The coil arrangement (1) according to claim 1, wherein the dipole capacitor (13a-d) has a suitable capacitance to tune the coil arrangement (1) to the first frequency.

17. The coil arrangement (1) according to claim 9, wherein a coupling element (14a-d) is connected in parallel with the dipole capacitor (13a-d), which is electrically connected to and bridges the two poles of the dipole antenna (2*a-d*), and wherein the coupling element (14*a-d*) is transferred from an electrically connecting state to an electrically disconnecting state, and vice versa, and wherein the coupling element (14*a-d*) is part of the junction device (11*a-d*).

18. The coil arrangement (1) according to claim 17, wherein the coupling element (14*a-d*) comprises a coupling element blocking circuit (15*a-d*), which automatically blocks when a high-frequency AC voltage with a frequency corresponding to the blocking frequency of the coupling element blocking circuit (15*a-d*) is applied to the coil arrangement (1), and wherein the blocking frequency of the coupling element blocking circuit (15*a-d*) corresponds to the first frequency.

19. The coil arrangement (1) according to claim 18, wherein at least one of the coupling element blocking circuits (15*a-d*) comprises a coupling element coil (16*a-d*) and a coupling element capacitor (17*a-d*), which are connected in parallel, and wherein the coupling element coil (16*a-d*) has an inductance from 38 to 41 nH, and/or the coupling element capacitor (17*a-d*) has a capacitance from 6 to 8 pF.

20. The coil arrangement (1) according to claim 19, wherein at least one coupling element (14*a-d*) comprises a second coupling element capacitor (18*a-d*) connected in series with the coupling element blocking circuit (15*a-d*) of the coupling element (14*a-d*), the second coupling element capacitor (18*a-d*) having a capacitance from 20 to 110 pF.

21. The coil arrangement (1) according to claim 1, wherein the second coupling element capacitor (18*a-d*) is configured to tune the coil arrangement (1) to the second frequency and/or to trigger a short circuit at the second frequency.

22. The coil arrangement (1) according to claim 20, wherein the dipole antenna arrangement (2) comprises four dipole antennas (2*a-d*), wherein the second coupling element capacitors (18*a-d*) of the coupling elements (14*a-d*) of the junction devices (11*a-d*) of two adjacent dipole antennas (2*a-d*) each have an equal capacitance of 33 pF, and the second coupling element capacitors (17*a-d*) of the two remaining dipole antennas (2*a-d*) have a capacitance of 95 pF or 100 pF.

23. The coil arrangement (1) according to claim 3, wherein the axial ends of the rod-shaped base element (8*a-d*) of at least one dipole antenna (2*a-d*) each connect to the respective conductor path segment (9*a-h*) of the dipole antenna (2*a-d*) with the interposition of a junction point capacitor (10*a-h*), the junction point capacitor (10*a-h*) having a capacitance from 10 to 40 pF.

24. The coil arrangement (1) according to claim 1, wherein the junction point capacitor (10*a-h*) is configured to tune the coil arrangement (1) to the second frequency.

25. The coil arrangement (1) according to claim 2, wherein the coil arrangement (1) is tuned by the second connecting element capacitors (7*a-h*) and/or the second coupling element capacitors (18*a-d*) and/or the dipole capacitors (13*a-d*) and/or the junction point capacitors (10*a-h*) such, and wherein each dipole antenna (2*a-d*) in the electrically disconnecting state of the connecting elements (3*a-h*) and the coupling elements (14*a-d*) can radiate and/or receive a high-frequency electromagnetic alternating field with a $^1$H-core resonant frequency, and wherein the volume coil resulting in the electrically connecting state of the connecting elements (3*a-h*) and of the coupling elements (14*a-d*) and/or each conductor loop (20*a-c*) of the conductor loop arrangement resulting in the electrically connecting state of the connecting elements (3*a-h*) and of the coupling elements (14*a-d*) can radiate and/or receive a high-frequency electromagnetic alternating field with an X-core resonant frequency.

26. The coil arrangement (1) according to claim 1, wherein each conductor loop (20*a-c*) of the conductor loop arrangement resulting in the electrically connecting state of the connecting elements (3*a-h*) and of the coupling elements (14*a-d*) is formed at least by parts of two adjacent dipole antennas (2*a-d*).

27. The coil arrangement (1) according to claim 26, wherein at least a part of a dipole antenna (2*a-d*) forms part of two adjacent conductor loops (20*a-c*) and the capacitance values of the connecting element capacitors (6*a-h*) and/or of the second connecting element capacitors (7*a-h*) and/or of the coupling element capacitors (17*a-d*) and/or of the second coupling element capacitors (18*a-d*) and/or of the dipole capacitors (13*a-d*) and/or of the junction point capacitors (10*a-h*) and/or of further capacitors within the conductor loop arrangement are configured so that adjacent conductor loops (20*a-c*) are decoupled.

28. A MR system having the coil arrangement (1) according to claim 1.

29. Use of the coil arrangement (1) according to claim 1 as a high-frequency transmitter and/or reception coil in magnetic resonance imaging.

* * * * *